US010282640B2

(12) United States Patent
Bonnier et al.

(10) Patent No.: US 10,282,640 B2
(45) Date of Patent: May 7, 2019

(54) APPARATUS AND METHOD FOR VISUALIZING TISSUE MACRO- AND MICROSTRUCTURE FOR PATHOLOGY EVALUATION IN MAGNETIC RESONANCE IMAGING

(71) Applicants: SIEMENS HEALTHCARE AG, Zurich (CH); CENTRE HOSPITALIER UNIVERSITAIRE VAUDOIS, Lausanne (CH)

(72) Inventors: Guillaume Bonnier, Crissier (CH); Cristina Granziera, Renens (CH); Tobias Kober, Lausanne (CH); Gunnar Krueger, Waertown-Boston, MA (US)

(73) Assignees: Siemens Healthcare GmbH, Zurich (CH); Centre hospitalier universitaire vaudois, Lausanne (CH)

(*) Notice: Subject to any disclaimer, the term of this patent is extended or adjusted under 35 U.S.C. 154(b) by 155 days.

(21) Appl. No.: 15/604,142

(22) Filed: May 24, 2017

(65) Prior Publication Data
US 2017/0344856 A1 Nov. 30, 2017

(30) Foreign Application Priority Data
May 24, 2016 (EP) .................... 16171060

(51) Int. Cl.
*G06K 9/62* (2006.01)
*G06K 9/52* (2006.01)
(Continued)

(52) U.S. Cl.
CPC .......... *G06K 9/6267* (2013.01); *A61B 5/0042* (2013.01); *A61B 5/055* (2013.01);
(Continued)

(58) Field of Classification Search
CPC ...... G06K 9/6267; G06K 9/52; G06K 9/4671; G06K 2209/051; A61B 5/055; A61B 5/0042; A61B 2576/026; A61B 5/1075
(Continued)

(56) References Cited

U.S. PATENT DOCUMENTS

2002/0173713 A1* 11/2002 Pfefferbaum .......... A61B 5/055
600/407
2009/0252391 A1 10/2009 Matsuda et al.
2014/0341471 A1 11/2014 Ono et al.

OTHER PUBLICATIONS

Lorio S. et al: "Disentangling in vivo the effects of iron content and atrophy on the ageing human brain"; NeuoImage; vol. 103; pp. 280-289; XP029093185.
(Continued)

*Primary Examiner* — Amandeep Saini
(74) *Attorney, Agent, or Firm* — Laurence Greenberg; Ralph Locher; Werner Stemer

(57) ABSTRACT

A method improves a detection of a brain tissue pathology in magnetic resonance (MR) images of a patient. The method includes acquiring multiple MR imaging data for creating four different contrast maps of a patient brain. From the multiple MR imaging data, performing an estimation of gray matter (GM), white matter (WM) and cerebrospinal fluid (CSF) concentration for each voxel of a part of the patient brain. From the multiple MR imaging data, segmenting the part of the patient brain in different regions-of-interest (ROIs) according to a chosen atlas. For each voxel of each of the contrast maps of the patient brain, computing, for the part of the patient brain, a deviation score. The method further includes creating from the deviation score and for each of the quantitative contrast maps, a deviation map representing the part of the brain in dependence on the deviation score calculated for each voxel.

8 Claims, 3 Drawing Sheets

(51) Int. Cl.
  *A61B 5/00*    (2006.01)
  *A61B 5/055*   (2006.01)
  *G06K 9/46*    (2006.01)
  *A61B 5/107*   (2006.01)

(52) U.S. Cl.
  CPC .............. *G06K 9/52* (2013.01); *A61B 5/1075* (2013.01); *A61B 2576/026* (2013.01); *G06K 9/4671* (2013.01); *G06K 2209/051* (2013.01)

(58) Field of Classification Search
  USPC ........................................................ 382/131
  See application file for complete search history.

(56) References Cited

OTHER PUBLICATIONS

Draganski B. et al: "Regional specificity of MRI contrast parameter changes in normal ageing revealed by voxel-based quantification (VBQ)"; NeuroImage; vol. 55 No. 4; pp. 1423-1434; XP028368088.

\* cited by examiner

APPARATUS AND METHOD FOR VISUALIZING TISSUE MACRO- AND MICROSTRUCTURE FOR PATHOLOGY EVALUATION IN MAGNETIC RESONANCE IMAGING

CROSS-REFERENCE TO RELATED APPLICATION

This application claims the priority, under 35 U.S.C. § 119, of European Patent Application EU 16171060.3, filed May 24, 2016; the prior application is herewith incorporated by reference in its entirety.

BACKGROUND OF THE INVENTION

Field of the Invention

The present invention relates generally to tissue macrostructure and microstructure visualization in Magnetic Resonance (MR) imaging.

MR imaging is known for its excellent soft tissue contrast. Today's clinical MR is based on a visual reading of relative intensity differences—creating the tissue contrast—in a qualitative manner. The image intensities of the different biological tissues obtained are the result of a complicated combination of the underlying physical parameters of these tissues, the acquisition method and its parameters as well as the employed hardware.

The essential physical parameters governing the MR contrast are T1 relaxation, T2 relaxation, T2* relaxation, and magnetization transfer. MR imaging techniques measuring these parameters provide valuable structural information about physiological and pathological properties of brain tissue. Notably, those physical tissue parameters are sensitive to different underlying biological processes and enable thus a deeper understanding of both healthy and pathological tissue. Biological properties influencing the MR-measurable parameters are, among others, the amount of free water protons, the degree of structural organization (i.e. amount of micro-molecules and macromolecules such as myelin, lipids, proteins), and the presence of paramagnetic substances (i.e. iron).

By combining multiple MR imaging data, it is possible to increase the specificity to brain tissue characteristics and their pathological changes in a neurological disease. Thanks to the development of fast and robust MR imaging sequences, it is today possible to acquire multiple MR images in a clinically compatible protocol. However, despite the rich content of the different parameter maps, their interpretation is difficult due to the enormous amount of information and the necessity to combine complementary information.

There have been previous attempts to combine diffusion tensor imaging (DTI) with magnetization transfer imaging (MTI) data or relaxometry (T1 or T2) acquisitions with MTI/DTI. In the field of neuroinflammatory and neurodegenerative diseases like multiple sclerosis and dementia, a number of previous studies combined parametric maps to study brain tissue pathology as explained for instance in the following publications:

Glasser, M. F. & Van Essen D. C., *Mapping Human Cortical Areas in Vivo Based on Myelin Content as Revealed by T1- and T2-Weighted MRI* (J Neurosci. 31, 11597-11616, 2011);

Grydeland, H. et al., *Intracortical Myelin Links with Performance Variability Across the Human Lifespan: Results from T1- and T2-Weighted MRI Myelin Mapping and Diffusion Tensor Imaging* (J Neurosci. 33, 18618-18630, 2013), or Draganski, B. et al., *Regional Specificity of MRI Contrast Parameter Changes in Normal Ageing Revealed by Voxel-Based Quantification (VBQ)* (NeuroImage 55, 1423-1434, 2011); and/or Lorio, S. et al., *Disentangling in Vivo the Effects of Iron Content and Atrophy on the Ageing Human Brain* (NeuroImage 103, 280-289, 2014).

Nevertheless, new approaches are still needed in order to improve the detection and quantification of brain tissue pathologies. It is therefore an objective of the present invention to provide a method and an apparatus for improving tissue macrostructure and microstructure visualization in MR images in order to ameliorate the detection and identification of brain tissue pathologies by a MR imaging apparatus operator.

SUMMARY OF THE INVENTION

This objective is achieved according to the present invention with respect to a new technique combining multi-parametric data for detecting brain tissue pathologies. In particular, said the technique combined quantitative information obtained by different intensity contrasts in a single colour-coded map where colors might then be associated with pathological processes (e.g. inflammation, degeneration, fibrosis, etc. . . . ), and where voxel intensity represents the deviation of tissue characteristics from healthy tissue, based on multiple MR-derived metrics, as it will be described in more details in the claimed method and apparatus.

Indeed, the present invention concerns in particular a method for detecting and quantifying a brain tissue pathology in MR images of a patient, the method being implemented by a MR imaging apparatus and containing the following steps:

1. Acquiring multiple MR imaging data, notably for contrast maps of a patient brain, and creating at least 4 different MR imaging contrast maps (hereafter simply called contrast maps) from said imaging data, notably T1, T2 and T2* relaxometry maps as well as Magnetisation Transfer Ratio (MTR) map, wherein the contrast maps are in particular quantitative contrast maps, for instance, T1, T2, T2* relaxometry quantitative contrast maps and a MTR quantitative contrast map.

2. From the acquired MR imaging data, performing an estimation of gray matter (GM), white matter (WM) and cerebrospinal fluid (CSF) concentration for each voxel of at least a part of the patient brain and creating, from the estimation, GM, WM and CSF concentration maps for said part of the patient brain.

3. From the acquired MR imaging data and/or optionally by using techniques such as MP2RAGE uni, 3DFLAIR, 3DDIR, extracting lesions and identifying brain tissues (WM, GM or mixed GM/WM) to create lesions mask wherein in particular each voxel intensity is zero except if it belongs to a WM lesion, GM lesion, mixed WM/GM lesion. The lesions extraction can be done manually or automatically according to the precision of the automatic technique used. Automatic detection of lesions is for example described in the articles Fartaria, M. J. et al., "Automated Detection of White Matter and Cortical Lesions in Early Stages of Multiple Sclerosis", J. Magn. Reson. Imaging (2015), and Datta, S., & Narayana, P. A., "A comprehensive approach to the segmentation of multichannel three-dimensional MR brain images in multiple sclerosis", Neuroimage Clin, 2, 184-196 (2013). Lesion automatic detection such as described in the previous articles might be use for the automatic lesion extraction and identification. Preferentially, the lesions mask are used for modifying WM, GM and CSF concentration maps according to the tissue type affected by lesions, creating therefore modified WM, GM and CSF concentration maps.

4. From acquired MR imaging data, for segmenting the part of the patient brain in different regions-of-interest (ROIs) according to a chosen atlas, e.g. lobes and hemispheres. Optionally and additionally, for each contrast map and for each ROI, the present method comprises a determination of parameter values characterizing the contrast map intensity distribution of each tissue (GM, WM, CSF) in healthy subjects based on an analysis of a group of healthy subjects. In this case, a same multiple MR imaging data as acquired previously for the patient brain have to be acquired for the healthy subjects.

5. For each voxel of each of the previously created contrast maps of the patient brain, computing, for at least the part of the patient brain, a deviation score (for example a z-score) obtained by combining:
   a) voxel intensity of the contrast map in the patient brain,
   b) either voxel tissues concentrations of GM, WM and CSF in the patient brain from the concentrations maps and optionally voxel information regarding lesions from the lesions mask, or preferentially voxel tissues concentrations of GM, WM and CSF in the patient brain from the previously modified WM, GM and CSF concentrations maps, and the parameters values characterizing the contrast map intensity distribution of each tissue in healthy controls (e.g. intensity mean, variance and covariances values of GM, WM and CSF) obtained for the ROI to which the voxel belongs to, and creating from the deviation score and for each of the previously created quantitative contrast maps, a deviation map representing the part of the brain in function of the deviation score calculated for each voxel. Based on a MR imaging database of healthy controls including MR imaging data as used in step 1, the parameters values characterizing the contrast map intensity distribution are extracted for each tissue, each brain ROI and each contrast (T1, T2, T2*, MTR). Advantageously, the combination is therefore configured for providing a voxel-wise description of focal and diffuse brain inflammation and degeneration through the deviation score;

6. Combining the previously obtained deviation maps (one for each contrast) into a single pathology map, e.g. a coloured pathology map. Preferentially, each voxel of the colored pathology map is a combination of deviation voxel (or score) intensities of each of the previously obtained deviation maps into a colour, where the color value identifies the pathology and its intensity characterizes the deviation (black for no deviation and intense colour for high deviation). In particular, the present method uses multivariate cluster analysis of contrast intensities space (e.g. a space where each direction correspond to each contrast) to identify the pathologies and associate a cluster to each pathology. Then the present method containing associating to each cluster a color, wherein the position of the deviations of the voxel in this cluster determines its intensity.

Preferentially, this new technique relies on brain tissue identification such as grey matter (GM), white matter (WM) and cerebrospinal fluid (CSF) in a single-patient and comparison with the parameters values characterizing the contrast map intensity distribution of each tissue of each ROIs and of each contrast obtained from the analysis of healthy subjects.

Advantageously, the claimed new technique does not suffer from limitations derived from inter-subject registration like in voxel-brain morphometry. Moreover, new technique includes preferentially tissues concentrations computed from a partial volume (PV) estimation algorithm (see for instance Roche A. et al., MICCAI 2014) applied on structural T1 data. It supports with WM and GM tissue concentration information, which is reliable also in areas where PV effects are important such as the cortical ribbon, the deep gray matter nuclei and the cerebellum. Deviation maps for each contrast are then preferentially presented with a colour-coded scheme.

Finally, the present invention also concerns a MRI apparatus for imaging an object, the MRI apparatus being configured for performing the method steps previously described. Preferentially, each step of the method is automatically performed, e.g. by the MR imaging apparatus, in a manner free of human intervention. Lesions detection and identification can be done manually for a better accuracy depending on precision of automatic technique used. For example, the present method proposes to use multichannel approaches developed by Fartaria, M. J. (*J. Magn. Reson. Imaging.* 2015) or Datta, S., (*Neuroimage Clin*, 2, 184-196. 2013) as explained before.

Other features which are considered as characteristic for the invention are set forth in the appended claims.

Although the invention is illustrated and described herein as embodied in an apparatus and a method for visualizing tissue macrostructure and microstructure for pathology evaluation in magnetic resonance Imaging, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
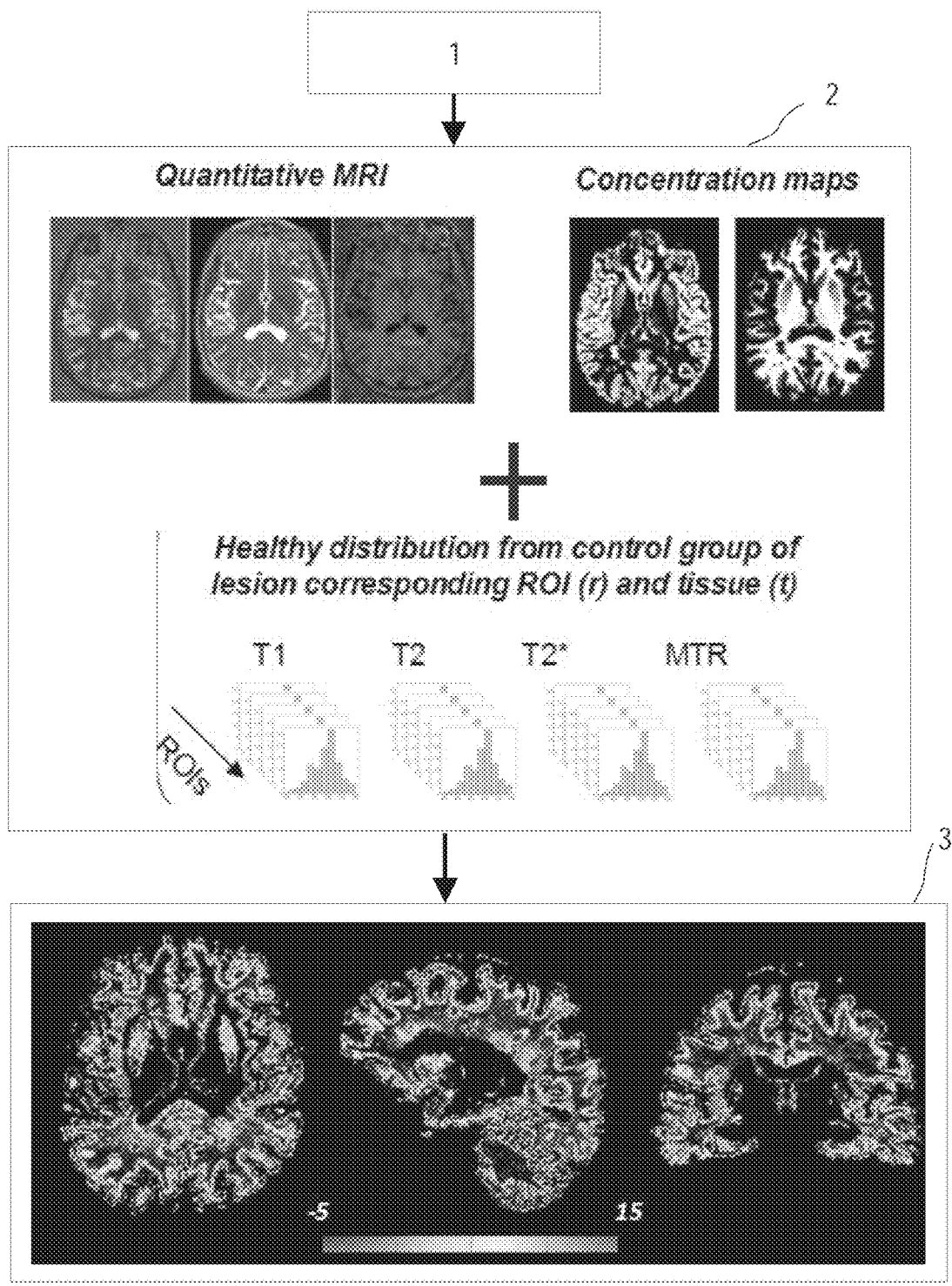
FIG. 1 is a flowchart for illustrating a method in accordance with a disclosed embodiment.

Referring now to the figures of the drawings in detail and first, particularly to FIG. 1 thereof, there is shown an illustration of a preferred embodiment of the claimed method that can be automatically performed by a MR imaging apparatus according to the present invention.

Figure 3:
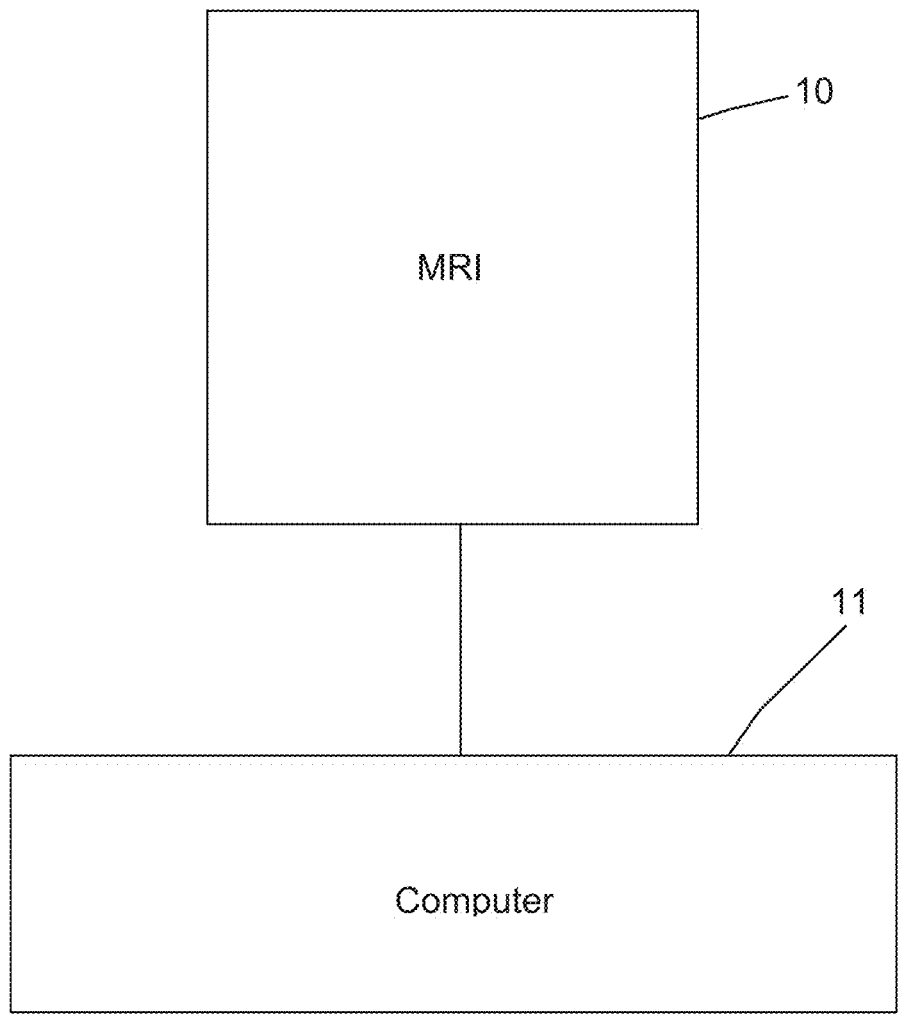
FIG. 3 is an illustration of an MRI machine.

According to a first step 1 of the disclosed method, multiple MR imaging data are acquired by the MR imaging apparatus 10 and its associated computer 11 (FIG. 3). The data are in particular used for automatically creating contrast maps of a patient brain by the MR imaging apparatus. Preferentially, the following quantitative contrast maps are automatically created by the MR imaging apparatus from the acquired multiple MR imaging data: T1, T2 and T2* relaxometry maps and a Magnetisation Transfer Ratio (MTR) map.

According to a second step 2, concentration maps are automatically created from the MR imaging data previously acquired in step 1. Preferentially, GM, WM and CSF concentration maps are automatically created by the MR imaging apparatus from acquired MR imaging data. According to a preferred embodiment, T1 quantitative contrast maps are used for creating the above-mentioned concentration maps.

According to a third step 3, lesions are detected and identified (WM, GM, mixed WM/GM). Preferentially, lesions are automatically detected and identified by the MR imaging apparatus from the acquired MR imaging data. For example, the multichannel approach developed by Fartaria, M. J. (*Automated Detection of White Matter and Cortical Lesions in Early Stages of Multiple Sclerosis. J. Magn. Reson. Imaging.* 2015) is used for implementing an automated detection system based on advanced MRI sequences based on the k-nearest neighbor (k-NN) classification. Another approach of Datta, S (*A Comprehensive Approach to the Segmentation of Multichannel Three-Dimensional MR Brain Images in Multiple Sclerosis. Neuroimage Clin, 2,* 184-196. 2013) might be used for automatically classifying tissues and lesions by integrating a brain anatomical knowledge with non-parametric and parametric statistical classifiers.

According to a step 3', the concentration maps are combined with lesions mask by changing the voxel of each concentration map (i) to 100% for WM concentration map, 0% for GM concentration map and 0% for CSF concentration map if the voxel belongs to a WM lesion, (ii) to 0% for WM concentration map, 100% for GM concentration map and 0% for CSF concentration map if the voxel belongs to GM lesion, and (iii) to 50% for WM concentration map, 50% for GM concentration map and 0% for CSF concentration map if the voxel belongs to GM/WM lesion.

According to a fourth step 4, the patient brain is automatically segmented in different ROIs (e.g. lobes, hemispheres). The segmentation is automatically performed by MR imaging apparatus from the acquired imaging data. For example, the present method uses the atlas based algorithm MorphoBox for segmenting regions of brain using MPRAGE images (Schmitter et al. *An Evaluation of VolumeBased Morphometry for Prediction of Mild Cognitive Impairment and Alzheimer's Disease* 2015).

According to an optional step 4', parameters values characterizing the quantitative contrast map intensity distribution in healthy subjects are determined for each quantitative contrast map, each ROI and each tissue.

According to a fifth step 5, for each of the quantitative contrast maps previously created, the MR imaging apparatus is configured for automatically combining (i) voxel intensity values of the quantitative contrast map representing the part of the patient brain with (ii) voxel intensity values of the previously modified concentration maps representing the part of the patient brain and with (iii) the parameter values characterizing the quantitative contrast map intensity distribution of each tissue in healthy subjects obtained from a group of healthy subjects for the quantitative contrast map and the ROIs into which the part has been automatically segmented.

For instance, according to the present invention, voxel intensity values of T1 quantitative contrast map might be combined with voxel intensity values of the GM, WM and CSF concentration maps representing the part of the patient brain and with the parameters values characterising the T1 quantitative contrast map intensity distribution of each tissue in healthy subjects that would be obtained for a T1 quantitative contrast map of the part of the brain when imaging a brain of a group of healthy subjects.

For instance, according to the present invention, voxel intensity values of MTR semi-quantitative contrast map might be combined with voxel intensity values of the GM, WM and CSF concentration maps representing the part of the patient brain and with the parameters values characterizing the MTR semi-quantitative contrast map intensity distribution of each tissue in healthy subjects that would be obtained for a MTR semi-quantitative contrast map of the part of the brain when imaging a brain of a group of healthy subjects.

For instance, according to the present invention, voxel intensity values of T2 quantitative contrast map might be combined with voxel intensity values of the GM, WM and CSF concentration maps representing the part of the patient brain and with the parameters values characterizing the T2 quantitative contrast map intensity distribution of each tissue in healthy subjects that would be obtained for a T2 quantitative contrast map of the part of the brain when imaging a brain of a group of healthy subjects.

For instance, according to the present invention, voxel intensity values of T2* quantitative contrast map might be combined with voxel intensity values of the GM, WM and CSF concentration maps representing the part of the patient brain and with the parameters values characterizing the T2* quantitative contrast map intensity distribution of each tissue in healthy subjects that would be obtained for a T2* quantitative contrast map of the part of the brain when imaging a brain of a group of healthy subjects.

In particular, the parameters values characterizing the contrast map intensity distribution (for example the quantitative contrast map intensity distribution) of each tissue in healthy subjects in each ROI of the MR imaging maps, such as the T1 quantitative contrast map, the T2 quantitative contrast map, the T2* quantitative contrast map, and the MTR semi-quantitative contrast map, might be stored in a database of the MR imaging apparatus and might be determined from MR imaging data acquired from a group of healthy subjects.

According to the fifth step 5, the MR imaging apparatus is configured for automatically creating, for each of the MR imaging maps of the patient brain part (i.e. for T1, and/or for T2, and/or for T2*, and/or for MTR quantitative MR imaging map) and according to the above-mentioned combination, a deviation map (i.e. one deviation map for T1, and/or another deviation map for T2, and/or another deviation map for T2*, and/or another deviation map for MTR), wherein the intensity $z_v$ of a voxel v of the created deviation map is the so-called deviation score and is a measure of a difference (and thus a deviation) between the voxel intensity value of said voxel in the imaging map for said part of the patient brain (for instance T1, and/or for T2, and/or for T2*, and/or for MTR quantitative MR imaging map) and the parameters values characterising the contrast map intensity distribution of each tissue of the healthy distribution for the voxel corresponding ROI (i.e. for T1, and/or for T2, and/or for T2*, and/or for MTR quantitative intensity properties of the same ROI but for a group of healthy subjects).

Preferentially, the MR imaging apparatus is configured for using the following equation for combining and creating the deviation map for each of the contrast maps, and in particular for each of the quantitative maps:

$$z_v = \frac{C_{GM}(I_v - \mu_{GM}) + C_{WM}(I_v - \mu_{WM}) + C_{CSF}(I_v - \mu_{CSF})}{(C_{GM}^2 \sigma_{GM}^2 + C_{WM}^2 \sigma_{WM}^2 + C_{CSF}^2 \sigma_{CSF}^2 + 2C_{GM}^2 C_{WM}^2 Cov_{GM/WM}^2 + 2C_{GM}^2 C_{CSF}^2 Cov_{GM/CSF}^2 + 2C_{WM}^2 C_{CSF}^2 Cov_{WM/CSF}^2)^{\frac{1}{2}}}$$ (Eq. 1)

wherein $C_{GM}$ is the intensity of the voxel in the GM concentration map;

$I_v$ is the intensity of the voxel in the contrast map;

$\mu_{GM}$ is a mean value of the healthy distribution of GM in the ROI where the voxel belongs to;

$C_{WM}$ is the intensity of the voxel in the WM concentration map;

$\mu_{WM}$ is a mean value of the healthy distribution of WM in the ROI where the voxel belongs to;

$C_{CSF}$ is the intensity of the voxel in the CSF concentration map;

$\mu_{CSF}$ is a mean value of the healthy distribution of the CSF in the ROI where the voxel belongs to;

$\sigma_{WM}$ is a standard deviation value of the healthy distribution of the WM in the ROI where the voxel belongs to;

$\sigma_{GM}$ is a standard deviation value of the healthy distribution of the GM in the ROI where the voxel belongs to;

$\sigma_{CSF}$ is a standard deviation value of the healthy distribution of the CSF in the ROI where the voxel belongs to;

$Cov_{GM/WM}$ is a covariance value of the healthy distribution between the GM and WM in the ROI where the voxel belongs to.

$Cov_{GM/CSF}$ is a covariance value of the healthy distribution between the GM and CSF in the ROI where the voxel belongs to.

$Cov_{WM/CSF}$ is a covariance value of the healthy distribution between the WM and CSF in the ROI where the voxel belongs to.

Figure 2:
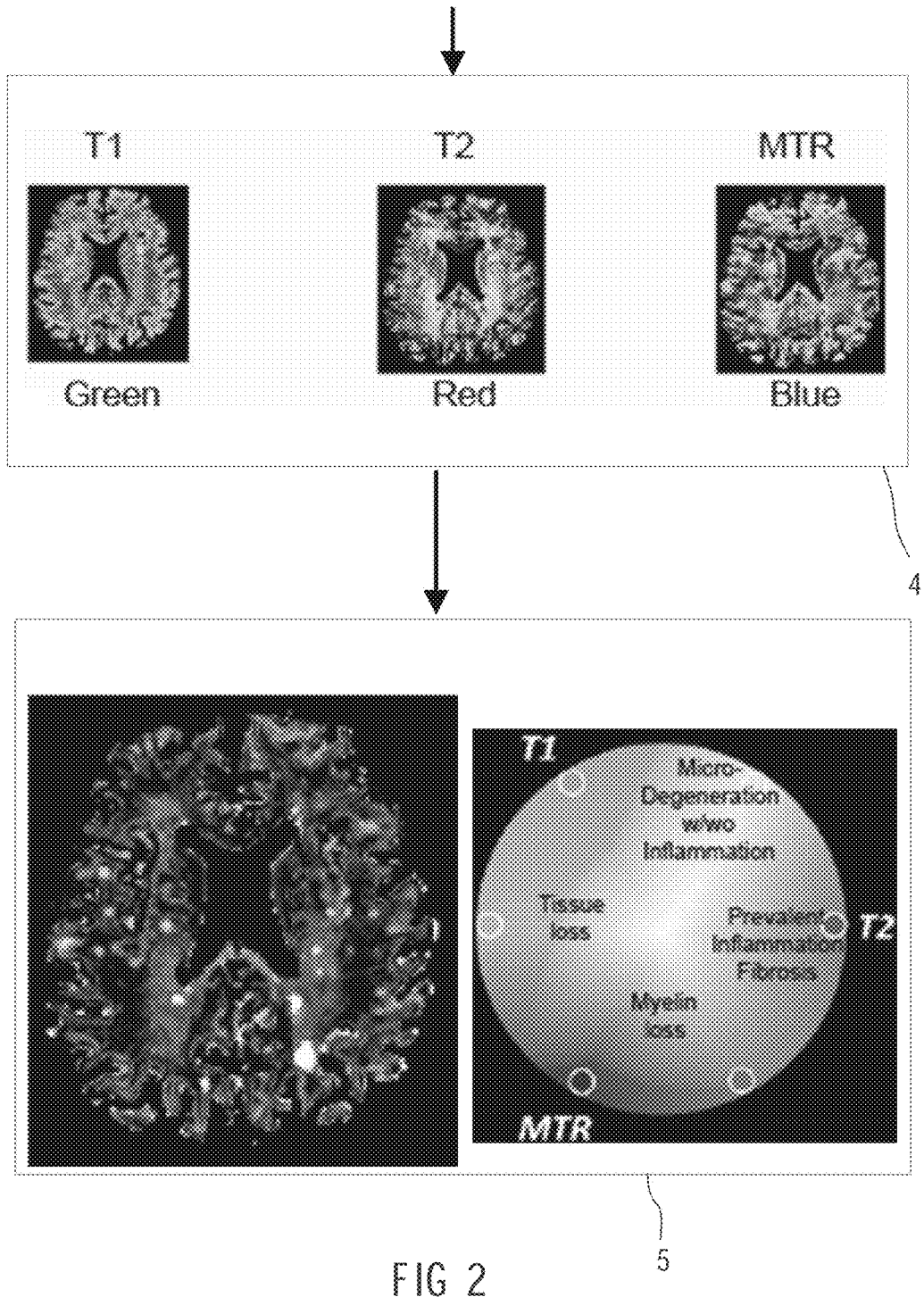
FIG. 2 is a continuation of the flowchart of FIG. 1 in accordance with the disclosed embodiment.

FIG. 2 illustrates the next step, i.e. step 4, of the preferred embodiment of the claimed method that can be automatically performed, preferentially by the MR imaging apparatus, according to the present invention. In particular, FIG. 2 shows three different deviation maps obtained respectively for T1, T2, and MTR quantitative contrast maps. According to the present invention, the MR imaging apparatus is further configured for automatically associating a color to each voxel from the intensities of this voxel in each deviation maps. In this example, the mapping is based on the combination of primary colors (green, red and blue respectively) associated to T1, T2 and MTR deviation maps. On the right of the box corresponding to step 4 is represented a map of pathological processes that are associated to each colour and automatically computed for each pathological map.

The combination of the 4 deviation scores (i.e. deviation values) of the voxel into a single color value and intensity can be more complex to improve the visualization and understanding of the pathological map. This last step requires advanced analysis of the deviation intensities to map pathologies (e.g. inflammation, tissue loss) with adequate colours.

According to the present invention, the automatic combination of T1, T2, T2* MR imaging relaxometry maps with MTR maps allows a fast and precise detection of a presence of inflammation and degeneration in the brain tissue and a determination of the entity of the inflammation. In particular, by combining according to the present invention four MR contrasts (namely T1, T2, T2* and MTR quantitative MR imaging maps) in a single pathological map, the rendering of brain tissue inflammation and degeneration is improved compared to maps based on single contrasts. In addition, since the method is based on tissue and region identification in each subject, it does not suffer from the limitations derived from inter-subjects registration as do approaches based on voxel-based morphometry. Additionally, the method integrates an algorithm disentangling white and grey matter tissue concentrations in regions affected by partial volume at the resolution used in clinical protocols. Unlike usual tissue concentration techniques, this algorithm assumes that all voxels in brain have a concentration of GM, WM and CSF, even if most of time two of these three concentrations are null; furthermore, the claimed method is very robust also in regions like the cerebellum and the cortex. Last, the combination of the four MR imaging maps in a single color-coded map of tissue pathology improves a direct visualization of different pathologies. According to the present invention, the color-coded map based on multiple MRI contrasts provides an easy and quick mean to assess the presence and severity of brain tissue inflammation and degeneration in a single patient.

The invention claimed is:

1. A method for detecting a brain tissue pathology in magnetic resonance (MR) images of a brain of a patient, which comprises the steps of:
    acquiring multiple MR imaging data and using the multiple MR imaging data for creating at least four different contrast maps of the brain of the patient;
    performing an estimation of gray matter (GM), white matter (WM) and cerebrospinal fluid (CSF) concentration for each voxel of at least a part of the brain from the multiple MR imaging data acquired;
    creating from the estimation, GM, WM and CSF concentration maps for the part of the brain;
    segmenting the part of the brain in different regions-of-interest (ROIs) according to a chosen atlas from the multiple MR imaging data acquired;
    computing, for each voxel of each the contrast maps created of the brain, for at least the part of the brain, a deviation score obtained by combining voxel intensity of a contrast map in the brain of the patient, voxel tissues concentrations from the GM, WM and CSF concentration maps in the brain, and parameters values characterizing a contrast map intensity distribution of each tissue in healthy controls obtained for the ROI to which the voxel belongs to;
    creating from the deviation score and for each of the contrast maps being quantitative contrast maps, a deviation map representing the part of the brain in dependence on the deviation score calculated for each said voxel; and
    combining deviation maps into a single pathology map.

2. The method according to claim 1, wherein the four contrast maps are T1, T2 and T2* relaxometry maps and a magnetisation transfer ratio (MTR) map.

3. The method according to claim 1, which further comprises extracting lesions and identifying brain tissues to create a lesions mask from the multiple MR imaging data.

4. The method according to claim 3, which further comprises using the lesions mask for modifying the WM, GM and CSF concentration maps by changing voxel concentrations in order to precisely identify a tissue type altered by the lesions.

5. The method according to claim 1, which further comprises performing a determination of the parameters values characterizing the contrast map intensity distribution of each said tissue in healthy subjects based on an analysis of a group of the healthy subjects.

6. The method according to claim 1, wherein the pathology map is a colored pathology map, wherein each voxel of the colored pathology map is a combination of deviation score intensities of each of previously obtained deviation maps into a color, where a color value identifies a pathology and its intensity characterizes a deviation.

7. The method according to claim 1, wherein the deviation score is given by:

$$z_v = \frac{C_{GM}(I_v - \mu_{GM}) + C_{WM}(I_v - \mu_{WM}) + C_{CSF}(I_v - \mu_{CSF})}{(C_{GM}^2 \sigma_{GM}^2 + C_{WM}^2 \sigma_{WM}^2 + C_{CSF}^2 \sigma_{CSF}^2 + 2C_{GM}^2 C_{WM}^2 Cov_{GM/WM}^2 + A + B)^{\frac{1}{2}}}$$

with $$A = 2C_{GM}^2 C_{CSF}^2 Cov_{GM/CSF}^2$$
$$B = 2C_{WM}^2 C_{CSF}^2 Cov_{WM/CSF}^2$$

wherein:

$C_{GM}$ is an intensity of a voxel in the GM concentration map;

$I_v$ is an intensity of the voxel in the contrast map;

$\mu_{GM}$ is a mean value of a healthy distribution of GM in the ROI where the voxel belongs to;

$C_{WM}$ is an intensity of a voxel in the WM concentration map;

$\mu_{WM}$ is a mean value of a healthy distribution of WM in the ROI where the voxel belongs to;

$C_{CSF}$ is a intensity of a voxel in the CSF concentration map;

$\mu_{CSF}$ is a mean value of a healthy distribution of the CSF in the ROI where the voxel belongs to;

$\sigma_{WM}$ is a standard deviation value of the healthy distribution of the WM in the ROI where the voxel belongs to;

$\sigma^{GM}$ is a standard deviation value of the healthy distribution of the GM in the ROI where the voxel belongs to;

$\sigma_{CSF}$ is a standard deviation value of the healthy distribution of the CSF in the ROI where the voxel belongs to;

$Cov_{GM/WM}$ is a covariance value of the healthy distribution between the GM and WM in the ROI where the voxel belongs to;

$Cov_{GM/CSF}$ is a covariance value of the healthy distribution between the GM and CSF in the ROI where the voxel belongs to; and $Cov_{WM/CSF}$ is a covariance value of the healthy distribution between the WM and CSF in the ROI where the voxel belongs to.

8. A magnetic resonance imaging apparatus for imaging an object, the magnetic resonance imaging apparatus, comprising:

an imaging unit; and a processor controlling said imaging unit, said processor configured to automatically detect a brain tissue pathology in magnetic resonance (MR) images of a patient by performing the following steps of:

acquiring multiple MR imaging data and using the multiple MR imaging data for creating at least four different contrast maps of a brain of a patient;

performing an estimation of gray matter (GM), white matter (WM) and cerebrospinal fluid (CSF) concentration for each voxel of at least a part of the brain from the multiple MR imaging data acquired;

creating from the estimation, GM, WM and CSF concentration maps for the part of the brain;

segmenting the part of the brain in different regions-of-interest (ROIs) according to a chosen atlas from the multiple MR imaging data acquired;

computing, for each voxel of each the contrast maps created of the patient brain, for at least the part of the brain, a deviation score obtained by combining voxel intensity of a contrast map in the brain, voxel tissues concentrations from the GM, WM and CSF concentration maps in the brain, and parameters values characterizing a contrast map intensity distribution of each tissue in healthy controls obtained for the ROI to which the voxel belongs to;

creating from the deviation score and for each of the contrast maps being quantitative contrast maps, a deviation map representing the part of the brain in dependence on the deviation score calculated for each voxel; and combining deviation maps into a single pathology map.

* * * * *